United States Patent [19]
Kreikebaum et al.

[11] Patent Number: 5,467,189
[45] Date of Patent: Nov. 14, 1995

[54] IMPROVED PARTICLE SENSOR AND METHOD FOR ASSAYING A PARTICLE

[75] Inventors: Gerhard Kreikebaum, San Bernardino; David L. Chandler, Highland, both of Calif.

[73] Assignee: Venturedyne, Ltd., Milwaukee, Wis.

[21] Appl. No.: 384,601

[22] Filed: Jan. 12, 1995

Related U.S. Application Data

[63] Continuation of Ser. No. 126,570, Sep. 27, 1993, abandoned, which is a continuation of Ser. No. 7,958, Jan. 22, 1993, abandoned.

[51] Int. Cl.$^6$ .................................................. G01N 15/02
[52] U.S. Cl. .......................... 356/336; 356/343; 356/339; 250/574
[58] Field of Search ................................. 356/335–343, 356/73, 301, 39, 317, 318, 244, 246; 250/574, 575, 222.2

[56] References Cited

U.S. PATENT DOCUMENTS

| | | | |
|---|---|---|---|
| 2,649,387 | 8/1953 | Parsons et al. | 117/65 |
| 2,775,159 | 12/1956 | Frommer | 88/14 |
| 3,045,123 | 7/1962 | Frommer | 250/218 |
| 3,248,551 | 4/1966 | Frommer | 250/218 |
| 3,614,231 | 10/1971 | Shaw | 356/336 |
| 4,045,125 | 8/1977 | Fargas | 350/166 |
| 4,140,395 | 2/1979 | Kreikebaum | 250/574 |
| 4,173,415 | 11/1979 | Wyatt | 356/336 |
| 4,189,236 | 2/1980 | Hogg et al. | 356/338 |
| 4,224,551 | 9/1980 | Liebegott | 313/323 |
| 4,245,910 | 1/1981 | Kälander | 356/338 |
| 4,273,443 | 6/1981 | Hogg | 356/343 |
| 4,281,924 | 8/1981 | Auer et al. | 356/73 |
| 4,422,761 | 12/1983 | Frommer | 356/338 |
| 4,523,841 | 6/1985 | Brunsting et al. | 356/73 |
| 4,606,636 | 8/1986 | Monin et al. | 356/338 |
| 4,724,313 | 2/1988 | French et al. | 356/203 R |
| 4,798,465 | 1/1989 | Knollenberg | 356/336 |
| 4,842,406 | 6/1989 | VonBargen | 356/336 |
| 4,893,928 | 1/1990 | Knollenberg | 250/574 |
| 4,942,305 | 7/1990 | Sommer | 250/574 |
| 4,943,159 | 7/1990 | Oetliker et al. | 356/73 |
| 5,011,286 | 4/1991 | Petralli | 356/343 |
| 5,043,591 | 8/1991 | Ludlow et al. | 250/574 |
| 5,084,629 | 1/1992 | Petralli | 250/573 |
| 5,127,729 | 7/1992 | Oetliker et al. | 356/338 |

*Primary Examiner*—Hoa Q. Pham
*Attorney, Agent, or Firm*—Jansson & Shupe, Ltd.

[57] ABSTRACT

The disclosure involves a particle sensor having a mirror cavity unobstructed by masks and the like. A light detector is at the mirror secondary focal point and well outside the mirror cavity. A variation includes a beam splitter and a secondary light detector to improve detection of larger particles. A second embodiment includes a pair of elliptical mirrors offset along the light beam. Light reflected by the second mirror represents only changes in laser power and light scattered by gas molecules. The resulting signal is subtracted from that produced by the first mirror to obtain a relatively "clean" signal useful to assay very small particles.

28 Claims, 14 Drawing Sheets

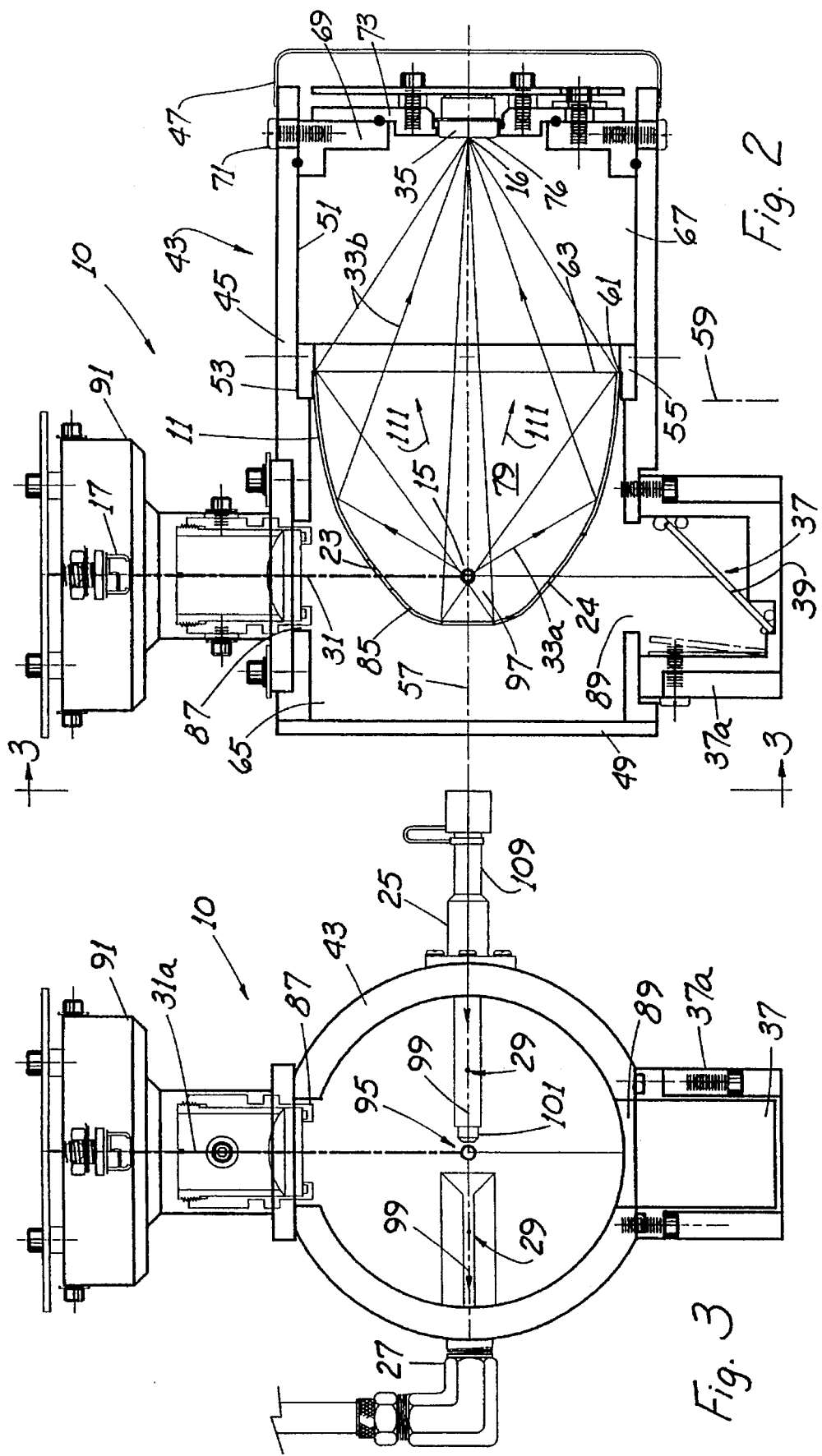

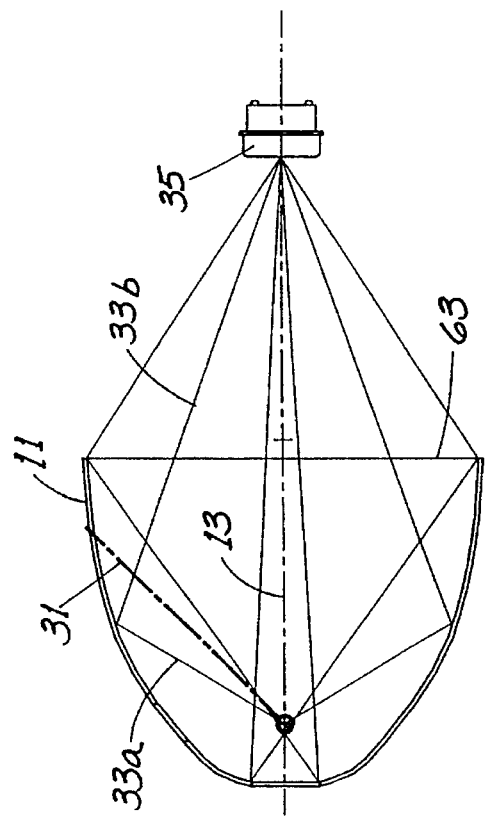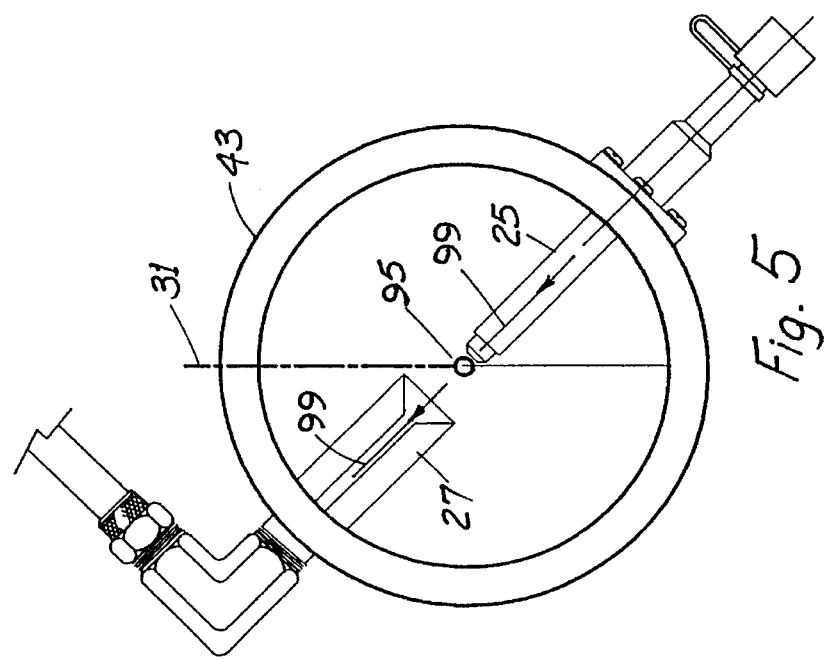

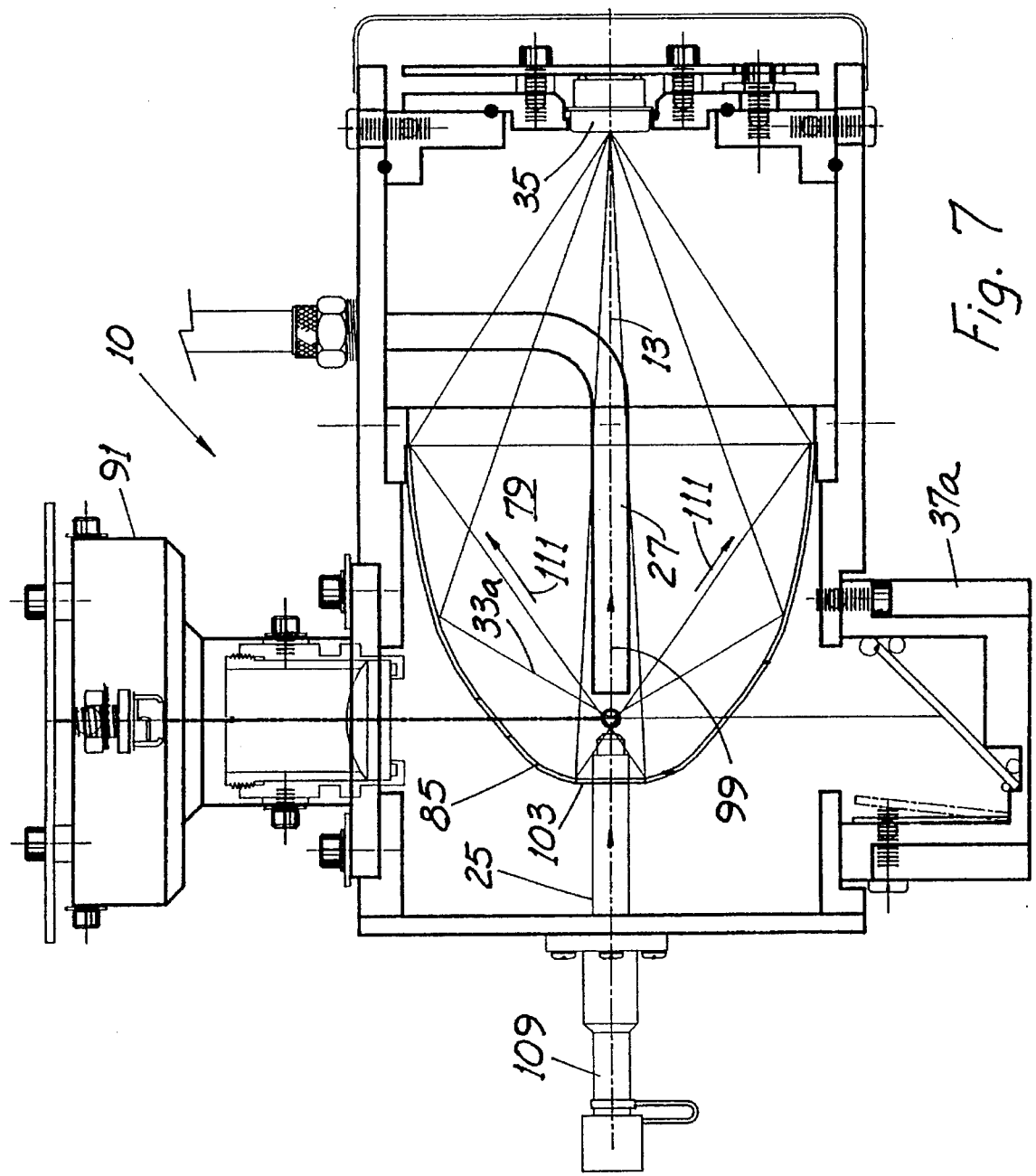

IMPROVED PARTICLE SENSOR AND METHOD FOR ASSAYING A PARTICLE

RELATED APPLICATIONS

This application is a continuation of now-abandoned application Ser. No. 08/126,570 filed on Sep. 27 1993 which is a continuation-in-part of now-abandoned application Ser. No. 08/007,958 filed on Jan. 22, 1993.

FIELD OF THE INVENTION

This invention relates generally to air quality and, more particularly, to instruments for assaying airborne particulates.

BACKGROUND OF THE INVENTION

Particle counters and sensors are used to detect light scattered by particles entrained in a stream of fluid, e.g., in an air stream. Such counters and sensors draw air (with entrained particles) from a room, for example, and flow such air along a tube and through an illuminated sensor "view volume" so as to obtain information about the number and size of such particles. Such information results from an analysis of the very small amounts of light "scattered" by the particle as it moves through the view volume.

Some types of sensors flow such air along an enclosed transparent tube; others "project" the air and accompanying particles at a particular flow rate (often measured in cubic feet per minute) from one tube across an open space to another tube. In sensors of the latter type, there is no tube wall (however transparent such wall may be) to impair light scattering and collecting. In other words, the particle is briefly illuminated by a very-small-diameter light beam as it "flies" through an open space.

Among other uses, particle counters incorporating particle sensors are used to obtain a measure of air quality by providing information as to the number and size of particles present in some specified volume of air, e.g., a cubic meter of air. Even work environments which appear to human observation to be clean—business offices, manufacturing facilities and the like—are likely to have substantial numbers of microscopic airborne particles. While such particles are not usually troublesome to the human occupants, they can create substantial problems in certain types of manufacturing operations.

For example, semiconductors and integrated chips are made in what are known as "clean rooms," the air in which is very well filtered. In fact, clean rooms are usually very slightly pressurized using extremely clean air so that particle-bearing air from the surrounding environs does not seep in. And the trend in the semiconductor and integrated chip manufacturing industry is toward progressively smaller products. A small foreign particle which migrates into such a product during manufacture can cause premature failure or outright product rejection even before it is shipped to a customer. This continuing "miniaturization" requires corresponding improvements in clean-room environments (and in the related measuring instruments) to help assure that the number and size of airborne particles are reduced below previously-acceptable levels. Known particle counters and sensors have not been entirely successful in this regard.

U.S. Pat. No. 4,606,636 (Monin et al.) patent describes a particle analyzing apparatus into which a particle is introduced through a tube-enclosed "view volume." A paraboloid reflector is shown, an ellipsoid reflector is described and the mirror cavity is obstructed by a mask. Particle-carrying tubes can refract light unpredictably and, often, the apparatus optical system is required to be more complex as a result. U.S. Pat. No. 4,523,841 (Brunsting et al.) shows a system used to measure aspects of biological cells. The system uses an ellipsoid reflector, a wide-area detector and a "cornucopia" type of light trap. U.S. Pat. No. 4,189,236 (Hogg et al.) patent shows a radiation collector used for analyzing aspects of blood cells and the like. Such collector uses light scattered by, e.g., a cell, and twice reflected before being received at a detector. U.S. Pat. No. 3,248,551 (Frommer) shows an optical arrangement for sensing very small particles such as dust or pollen.

Another disadvantage of known particle counters and sensors becomes manifest when trying to detect very small particles, e.g., 0.1 micron and smaller, and/or when trying to detect particles present in a relatively high-flow-volume, e.g., one cubic foot per minute, air stream. Because the particle is very small and/or because it is moving relatively rapidly (thus passing quickly through the illuminated view volume), such particle reflects and scatters very little light. The quantum of such light which can be detected and accurately measured is often near or below the resolution and sensitivity limits of existing sensors and detectors. And, of course, the latter produces a low level of inherent "noise."

An apparent solution is to increase the quantum of light reflected and scattered by a very small and/or fast-moving particles by increasing the intensity of the light beam. Such efforts have proven largely counterproductive since a more intense light source produces higher levels of random electronic or "shot" noise. And as the light beam becomes more intense, the quantum of light scattered by gas molecules tends to increase, irrespective of whether a particle is also present in the view volume. Shot noise and the increasing quanta of light scattered by gas molecules tends to partially or totally obscure the effect of the particle-scattered light.

To complicate matters even further, laser light sources tend to vary, even if only slightly, in output power during operation. As a consequence, the quantum of light scattered by gas molecules varies with variations in power. For high powered lasers used to detect very small particles at high flow rates, such variations can be of magnitudes much higher than the shot noise or the noise inherent in an electronic detector. These phenomena dramatically limit the attainable sensitivity.

An improved particle sensor which collects and analyzes a high percentage of light scattered by a very small particle and which helps neutralize the effect of light source power variations and gas molecule light scattering would be an important advance in the art.

SUMMARY OF THE INVENTION

The invention is an improvement in a particle sensor of the type having an elliptical mirror with a cavity, a major axis and primary and secondary focal points along that axis. The sensor includes a particle-illuminating beam of light having a wavelength and extending along a beam axis intersecting the primary focal point. An inlet tube introduces particles into a sensor "view volume" and an outlet tube recovers the particles which have passed through the view volume.

In the improved sensor, the mirror cavity is unobstructed by masks and the like and a primary light detector is at the secondary focal point well outside the mirror cavity. This light detector is "optimized" for detecting low-energy light like that scattered by very small particles when such particles pass through the light beam. More specifically, the sensor detects particles down to about 0.05 micron in size.

The particles pass through the view volume, i.e., a very small, generally cylindrical region where the light beam and particle path intersect. In the improved sensor, the view volume is a free-boundary spatial region, i.e., a region not bounded by walls of a particle-carrying tube or similar structure. The particle "flies" through this region projectile-like rather than being guided therethrough by a tube. When the sensor is so arranged, particles having a maximum dimension substantially less than the light wavelength are efficiently detected.

In the improved sensor, the beam axis and the major axis of the mirror define an included angle of about 90° and, preferably, such axes are at 90° with the particle path; that is, the axes and the path are orthogonal. However, the axes and the path need not be normal to one another; slight non-perpendicularity can be used. That is, the path and the beam axis may define an included angle of less than 90° as may the path and the mirror major axis, the two axes and/or both axes and the path.

In a highly preferred version, the sensor has an extended particle-detection range. That is, it can detect particles larger than those sized at about 60–65% of the beam wavelength such as are detected by the primary detector. Accordingly, the sensor may also include a beam splitter plate and a secondary detector. The secondary detector receives light reflected from the splitter plate, thereby improving the ability of the sensor to detect larger particles. Preferably, the splitter plate and the secondary detector are coincident with the mirror major axis and the splitter plate is between the detectors.

A light trap "captures" that light which does not strike a particle and is therefore not reflected by such particle. In another aspect of the invention, the light trap comprises a primary plate absorbing light of the wavelength of the beam. In a highly preferred embodiment, the plate comprises a light bandpass filter having a nominal bandpass wavelength range and the wavelength of the beam of light is outside such wavelength. A secondary plate may also be included to absorb those very small amounts of light reflected from the primary plate.

It has been found that if light "trapping" is performed outside the mirror cavity, there is a reduction in the amount of stray light which might otherwise create electronic "noise" in the detector circuitry. Accordingly, the light trap, whether of one or two plates, is outside the cavity. At least the primary plate is angularly oriented with respect to the beam axis to help prevent non-absorbed light from being reflected back into the cavity.

A second embodiment of the inventive sensor is particularly useful in detecting and assaying (determining, e.g., the size and number of) very small particles, especially those entrained in a high flow rate air stream. In the second embodiment, the sensor has a first apparatus collecting light scattered by an airborne particle and by gas molecules and also has a second apparatus collecting light scattered substantially only by gas molecules.

The first apparatus includes an elliptical light-reflecting first mirror having a major axis and the primary focal point substantially coincident with the view volume. The sensor has first and second detectors, one for each apparatus. Light reflected by the mirror impinges on the first detector which provides a first output signal and light collected by the second apparatus impinges on the second detector which provides a second output signal. The sensor includes a circuit subtracting the signals.

In a variant of the second embodiment, the second apparatus comprises an imaging system having at least one lens. Such lens collects light scattered by an airborne particle and by gas molecules. The detector of the second apparatus has a central portion and an opaque mask preventing a part of the lens-collected light from striking the central portion. As is explained in the detailed description, the light which is "blocked" by the mask is that which is reflected by a particle and by gas molecules rather than light which is reflected substantially only by gas molecules. The latter is allowed to impact the detector.

In another variant of the second embodiment, the second apparatus comprises a second mirror (preferably elliptical with a major axis) having a focal point displaced from the view volume, preferably displaced along the light beam axis. The second mirror reflects light scattered by gas molecules. The sensor has first and second detectors and in a highly preferred arrangement, the first detector is coincident with the major axis of the first mirror and the second detector is coincident with that of the second mirror.

As to further aspects of the sensor of the second embodiment, the first light detector receives light scattered by an airborne particle and by gas molecules while the second light detector receives light scattered substantially only by gas molecules and reflected by the second mirror. Each detector produces an output signal (first and second signals, respectively) and both such output signals include components resulting from (a) shot noise (explained below), (b) random detector noise and (c) changes in laser power. A subtraction circuit subtracts from the first output signal that component of the second output signal resulting from changes in laser power.

As explained in greater detail below, laser light sources do not provide light at an absolutely constant intensity. This is so since the laser power varies, perhaps by only a fraction of a percent, and light intensity varies with it. The light received by the first detector (scattered by a particle and by gas molecules) and that received by the second detector (scattered only by gas molecules) both evidence, by the same changes in "scattering signal" strength, such variations in laser power.

The signals from the detectors are processed in the subtraction circuit to eliminate (from that resultant signal which is to be analyzed) the variations in scattering signal strength. As its name suggests, the circuit does so by "subtracting out" the signal resulting from the light scattered only by gas molecules. Such circuit thus provides an output signal which is substantially devoid of variations in scattering signal resulting from changes in laser power. That is, such output signal represents (with minor exceptions explained below) substantially only light scattered by an airborne particle.

More specifically, the improved particle sensor of the second embodiment has a particle flow path which intersects the light beam axis and thereby defines a view volume with such axis. The general shape of such view volume is illustrated in the drawing.

Preferred mirrors are elliptical, each having a major axis and a primary and secondary focal point. The mirror major axes are preferably substantially parallel to one another. In a highly preferred arrangement of the second sensor embodiment, the first and second detectors are substantially at the secondary focal points of the first and second mirrors, respectively.

Other aspects of the invention involve a method for assaying a particle illuminated by a light beam. Such method includes the steps of collecting a first quantum of light scattered by a particle and by gas molecules and collecting a second quantum of light scattered substantially only by gas molecules. The first quantum of light, which is scattered at a first locus such as at the view volume, is collected by reflecting it from the first mirror, a focal point of which is preferably at the first locus. The second quantum of light, which is scattered at a second locus, is collected by reflecting it from the second mirror, a focal point of which is preferably at such second locus.

The method also includes the steps of generating a first signal representing the first quantum of light, generating a second signal representing the second quantum of light and subtracting the signals to obtain a "clean" output signal representing substantially only light scattered by a particle to be assayed.

The first signal generating step preferably includes the step of positioning an elliptical first mirror having a primary and a secondary focal point in a way that the first mirror reflects scattered light to a first detector at the mirror's secondary focal point. Similarly, the second signal generating step preferably includes the step of providing an elliptical second mirror having a primary and a secondary focal point and positioning such mirror in a way that the second mirror reflects scattered light to a second detector at the mirror's secondary focal point.

It is to be appreciated that while elliptical mirrors are preferred, other types of reflective light-collecting systems having suitable focusing or imaging properties may be used in practicing the invention and such systems are considered to be within the scope of such invention. Further details of the invention are set forth in the following detailed description taken in conjunction with the drawing.

OBJECT OF THE INVENTION

It is an object of this invention to provide an improved particle sensor overcoming some of the problems and shortcomings of the prior art.

Another object of this invention is to provide an improved particle sensor which helps detect very small airborne particles.

Yet another object of this invention is to provide an improved particle sensor which helps detect very small airborne particles using once-reflected light, thereby improving signal strength.

Another object of this invention is to provide an improved particle sensor which has an extended range for detecting larger airborne particles.

Yet another object of this invention is to provide an improved particle sensor which detects particles of a fraction of a micron in size.

Another object of this invention is to provide an improved particle sensor which helps negate the effect of variations in laser output power.

Yet another object of this invention is to provide an improved particle sensor having improved smallparticle sensitivity.

Still another object of this invention is to provide an improved particle sensor which efficiently traps unreflected light.

How these and other objects are accomplished will be apparent from the following descriptions taken in conjunction with the drawing.

BRIEF DESCRIPTION OF THE DRAWING

FIG. 2 is a cross-sectional view of the improved sensor taken from the perspective of viewing axes 2—2 of FIG. 1 and including certain housing components and omitting other components for clarity.

FIG. 3 is an end elevation view of the improved sensor taken from the perspective of viewing axes 3—3 of FIG. 2.

FIG. 5 is a view of the improved sensor, similar to the view of FIG. 3, and illustrating angular relationships described in the specification.

FIG. 6 is a view of the improved sensor, similar to the view of FIG. 2, and illustrating angular relationships described in the specification.

FIG. 7 is a cross-sectional side elevation view of the improved sensor similar to that of FIG. 2 and illustrating another variant of the first embodiment of the sensor.

DETAILED DESCRIPTION OF PREFERRED EMBODIMENTS

Figure 1:
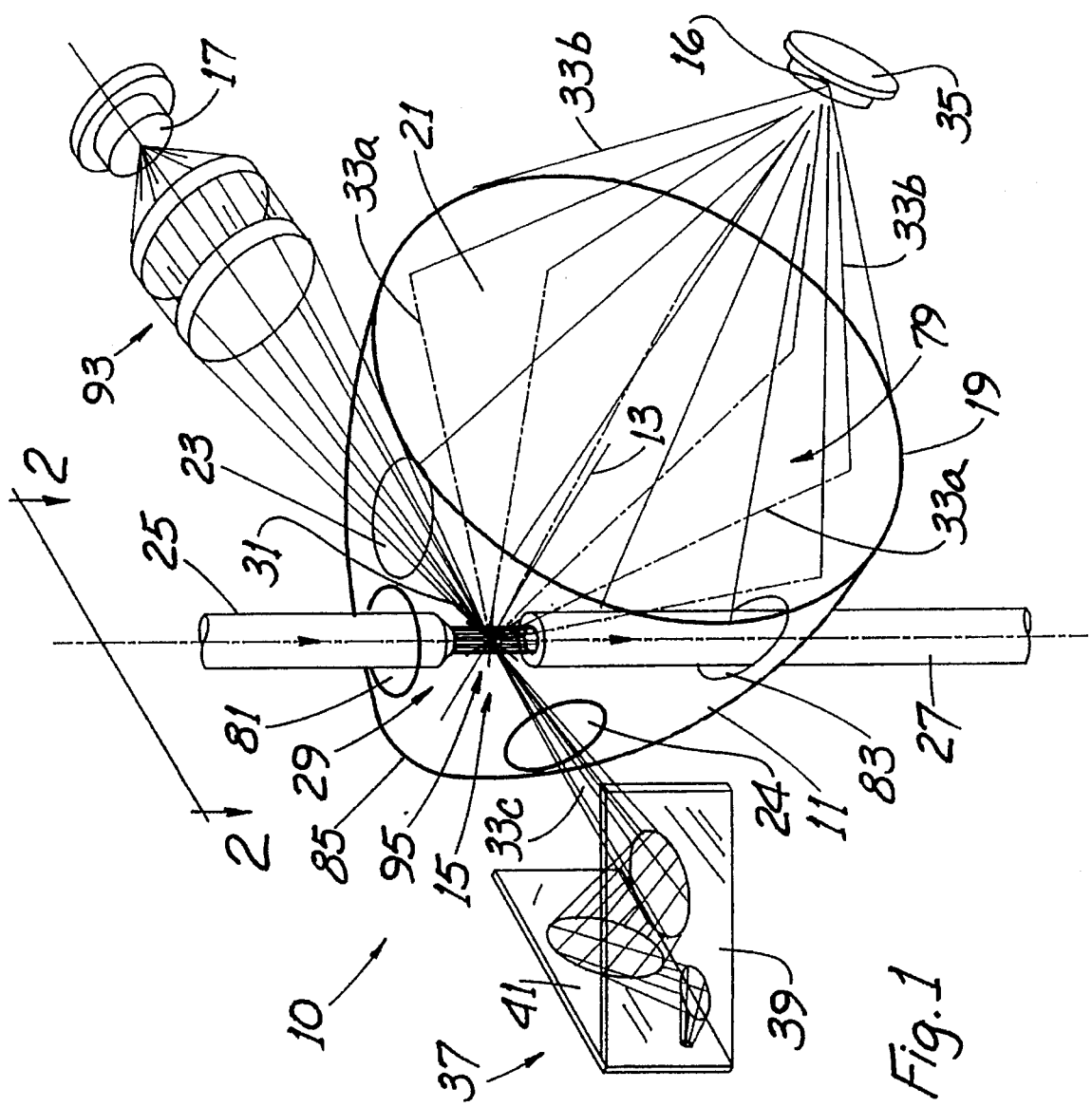
FIG. 1 is an isometric spatial representation of certain aspects of the improved sensor, with parts omitted.

Understanding of the embodiments of the improved sensor 10 will be aided by referring first to FIGS. 1–6 and, particularly, to FIG. 1 which shows certain components of the sensor 10 as if they were suspended in space. After appreciating the relative location of those components, the portrayals in the remaining Figures will be more readily understood.

The sensor 10 includes an elliptical mirror 11 having a mirror major axis 13, a primary focal point 15 and a secondary focal point 16. In FIG. 1, the mirror 11 is made to appear transparent for ease of understanding; in fact, its wall 19 is rigid and opaque and its interior surface 21 is highly reflective. Light from a light source 17 passes through a beam entry aperture 23 in the wall 19 of the mirror 11. Simultaneously, sample air (drawn from a room, for example) flows through the inlet tube 25 to the outlet tube 27. Any particle 29 entrained therein passes through the light beam 31 and scatters light 33a to the mirror reflective surface 21. Light 33b once-reflected by the mirror 11 converges at the primary detector 35 and the resulting electrical signal is analyzed to provide assay information about the particle 29 and others like it, e.g., particle size and "count" per volumetric measure of air. Light 33c not scattered by the particle 29 is "killed" by a light trap 37 having primary and secondary plates 39, 41, respectively. In a second embodiment of the sensor 10 (described below), the trap 37 is replaced by a reflective output mirror in a helium-neon active cavity laser.

Referring particularly to FIGS. 2,3,7 and 8, the improved particle sensor 10 includes a somewhat elongate, generally cylindrical, hollow body 43 having a body wall 45 and front and rear covers 47 and 49, respectively. The interior surface 51 of the wall 45 includes a stepped portion 53 against which a mirror support ring 55 is abutted. The stepped portion 53 is concentric with the long axis 57 of the body 43 and defines a circle, the plane 59 of which is generally normal to such axis 57.

The ring 55 is snugly received in the body 43 to prevent relative ring-body movement and includes a step-like, generally circular shoulder 61 diametrically sized to receive and securely hold the elliptical mirror 11 at its front edge. Like the portion 53, the shoulder 61 is concentric with the long axis 57 of the body 43 and defines a circle, the plane of which is generally normal to the axis 57. The mirror includes a major axis 13 which is generally coincident with the axis 57. But for some relatively small apertures described below, the mirror 11 divides the interior of the body 43 into a rear space 65 and a front space 67.

The mirror 11 has a primary focal point 15 and a secondary focal point 16, both of which are coincident with the axes 13 and 57. Understanding of the following aspects of the specification will be aided by brief mention of a known characteristic of an elliptical mirror 11. Such a mirror 11 has two focal points (like focal points 15, 16) along its major axis 13. Light rays 33a scattered at the primary focal point 15 will be reflected to the secondary focal point 16. In one preferred embodiment, the mirror 11 is called a "full generation, half reflector" mirror. That is, its interior reflective surface 21 is generally defined (but for some small openings like apertures 23, 24, 103 formed therein) by rotating or "generating" an ellipse through 360° about the axis 13 and then dividing the resulting shape (resembling the shape of a football) in half along the plane 63, i.e., along a plane perpendicular to the axis 13 and positioned halfway between the surface ends. It is to be appreciated that the mirror 11 need not be a full generation mirror. That is, one or more mirror segments, each of less than 360° generation (and of course aggregating to not more than 360° generation), may be used in place of the full generation mirror 11.

Mounted within the front space 67 of the body 43 are plural support brackets 69, each of which is affixed to the body 43 by one or more threaded fasteners 71. Each bracket 69 has a radially-inwardly projecting arm and such arms cooperate to support a detector mounting assembly 73 which includes a primary light detector 35. The brackets 69, assembly 73 and detector 35 are cooperatively arranged so that the sensing face 76 of the detector 35 is coincident with the secondary focal point 16, is generally normal to the axes 13, 57 and is positioned rearward-facing to pick up light 33b once-reflected from the mirror surface 21. And the arrangement is such that the sensing face 76 can be adjustably moved to the aforedescribed position while yet maintaining a slight vacuum within the body 43.

It should be appreciated that detector 35 and/or detector 77 may be configured to receive and react to light received over a relatively larger area or such a detector which is "point-like." As used in this specification, the term "point-like" refers to a detector (like detector 35 or secondary detector 77) which has been "optimized" to detect light received on the face 76 in a very small "impact area" approaching or approximating a point. A point-like detector is preferred for use in the sensor 10 in many applications since such detectors tend to operate faster, produce lower background noise and, frequently, are less expensive.

The detector 35 is also optimized to generate a voltage signal upon receipt of light having a wavelength of about 0.8 microns or shorter and, preferably, optimization is with respect to a specific light wavelength. It should be appreciated that the detector 35 is connected to an electronic circuit (not shown) which uses the detector voltage to provide information relating to particle size and quantity. A preferred detector 35 is a solid state photodiode for IR light sources or a photomultiplier tube for blue/green light sources.

In one preferred embodiment, the mirror 11 includes a pair of beam apertures 23, 24 through which the light beam 31 respectively enters and exits the mirror cavity 79. As further described below, such apertures 23, 24 are in registry with the light beam 31 emanating and extending from the light source 17 to the light trap 37. The mirror 11 also includes a pair of tube apertures 81, 83 through which the inlet tube and the outlet tube 25 and 27, respectively, extend.

Near the rather sharply curved end 85 of the mirror 11, the body 43 includes a source opening 87 and a trap opening 89. These openings 87, 89 are in registry with the light beam axis 31a extending through the body 43 and through the mirror primary focal point 15. A light assembly 91 is mounted adjacent to the opening 87 and has a light source 17 supported therein along with some optical focusing device, e.g., a suitable lens arrangement 93. The assembly 91 itself and the juncture of the assembly 91 and the body 43 are "light tight" so that no light can enter the body 43 to interfere with particle detection and counting.

For many applications, a laser diode is the preferred source 17 because it is relatively small in size, runs at low power levels, is relatively inexpensive and has output characteristics resulting in a generally uniform light intensity in the viewing volume 95 as further described below. Merely to cite some examples of products used for the light source 17 (the origin of the reflected light 33b which is sensed at the detector 35), today's infrared laser diodes emit light having a wavelength of about 0.78 microns, helium/neon lasers emit light of about 0.63 microns wavelength and light from an argon laser has a wavelength of about 0.5 microns.

And the invention is not limited to use only with those light sources 17 and detectors 35, 77 described herein.

Figure 9:
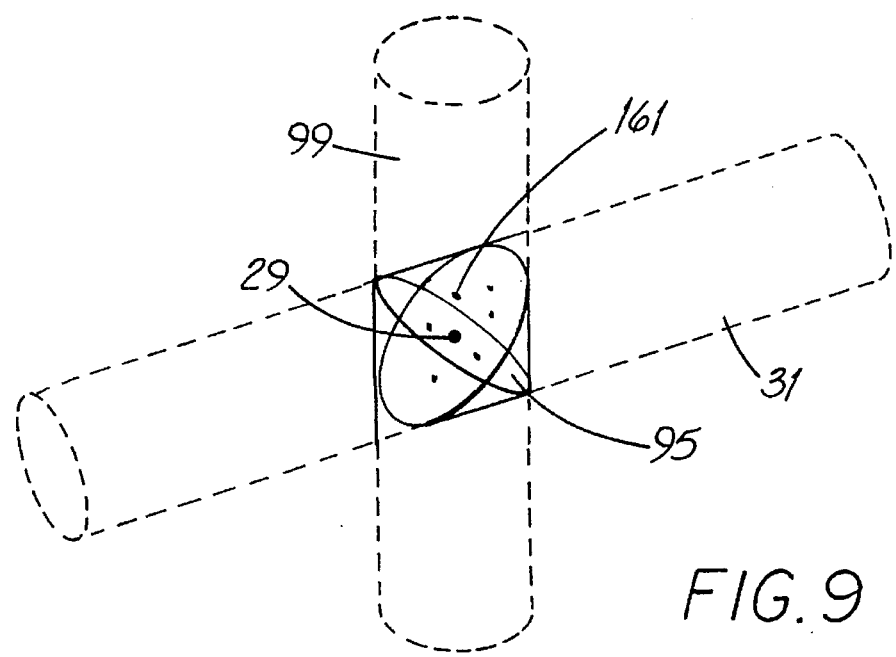
FIG. 9 is a spatial view showing the intersection of a light beam and a particle path to form a view volume. The beam and path are shown in dashed outline and are abbreviated in length.

Advances are continually being made in both and sources and detectors of other types are and will be considered to be within the scope of the invention. Considering FIG. 1, light from the source 17 is focused so that the light focal point 97 is coincident with the mirror primary focal point 15 and with the view volume 95. The greatly enlarged view of FIG. 9 helps understand the general shape of the view volume 95 which results from the intersection of the light beam 31 and the air flow defining a particle path 99. In FIG. 9, a particle 29 is represented by a larger dot while gas molecules 161 adjacent to the particle 29 are represented by smaller dots.

A light-tight trap assembly 37a is mounted at the trap opening 89 and includes the light trap 37. The improved sensor 10 uses a trap 37 that is believed to be unique and is highly effective. The trap 37 is preferably embodied as a primary plate 39 which absorbs light at a wavelength or within a range of wavelengths which includes the wavelength of the light emitted by the source 17. In a highly preferred embodiment, the plate 39 is a light bandpass filter made of glass about 1 mm thick but used in other than the intended manner.

Figure 4:
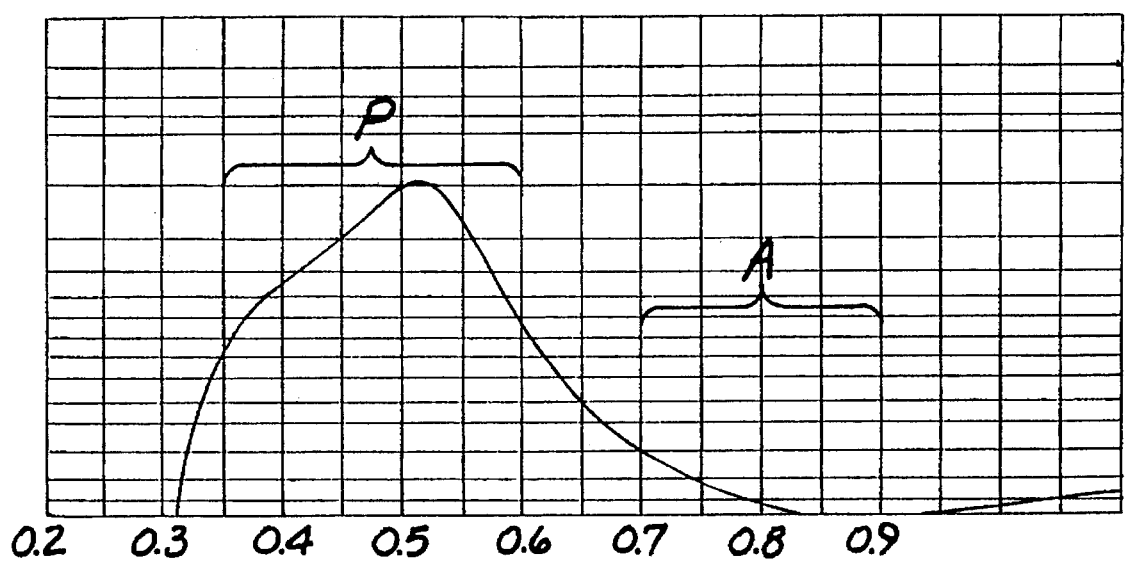
FIG. 4 is a graphical representation of the characteristics of a band pass light filter.

As an example and referring to FIG. 4, one bandpass filter is configured to have a nominal "pass band" range of 0.35 to 0.6 microns as represented by the bracket "P." That is, most of the light within the pass band range passes through the filter upon striking it. On the other hand, most light having a wavelength in the 0.7–0.9 micron range (as represented by bracket "A") is absorbed by the filter rather than passing through it.

The plate 39 is outside the cavity 79 and is angularly oriented with respect to the beam axis 31a. In other words, the plate 39 is non-perpendicular to such axis 31a. Such plate location and orientation provides substantial advantages. By locating the trap 37 outside the cavity 79, any light reflected from the plate 39 (which in any event is a very small amount of light) has virtually no opportunity to re-enter the cavity 79 and create spurious light signals. Such signals can result in electrical "noise" in the electronic detector circuit. And angular orientation helps avoid re-directing reflected light back into the cavity 79.

In another preferred arrangement, the light trap 37 also includes a secondary plate 41 absorbing light reflected from the primary plate 39. Since the purpose of the trap 37 is to "kill" light 33c which does not strike a particle 29, the secondary plate 41 is also selected to absorb light of the wavelength of the beam 31.

Referring further to FIG. 3, the inlet tube 25 and outlet tube 27 provide a path 99 along which airborne particles 29 travel for analysis. As each particle 29 exits the distal end 101 of the tube 25, it passes through the view volume 95 and is drawn (by slight vacuum in the outlet tube) into the outlet tube 27 for ultimate disposal. In that version of the sensor 10 shown in FIGS. 1, 2 and 3, the path 99 defines an included angle of about 90° with the beam axis 31a and the major axis 13 and the path 99 and the axes 13, 31a are thereby said to be orthogonal. However, the improved sensor 10 is operable even though the axes 13, 31a and the path 99 are not orthogonal. That is, any two or all of the axes 13, 31a and the path 99 may define an included angle of somewhat less than 90° therebetween and still fall within the scope of the invention. Such relationship is represented in a greatly exaggerated way by FIGS. 5 and 6.

In a variant of the first embodiment, shown in FIG. 7, the inlet tube 25 and the outlet tube 27 both project into the cavity 79, the former through a small aperture 103 at the mirror end 85. Like the particle path 99 provided by them, the tubes 25, 27 are coincident with the mirror major axis 13. The tubes 25, 27 are of sufficiently small diameter that they do not obstruct the cavity 79 and, particularly, do not materially obstruct light rays 33a scattered by a particle 29. It is to be understood that connections of the tubes 25, 27 and other hardware to the body 43 is, like the attachment 37a, 91 of the assemblies, in such a way that ambient light cannot enter the body 43.

Figure 8:
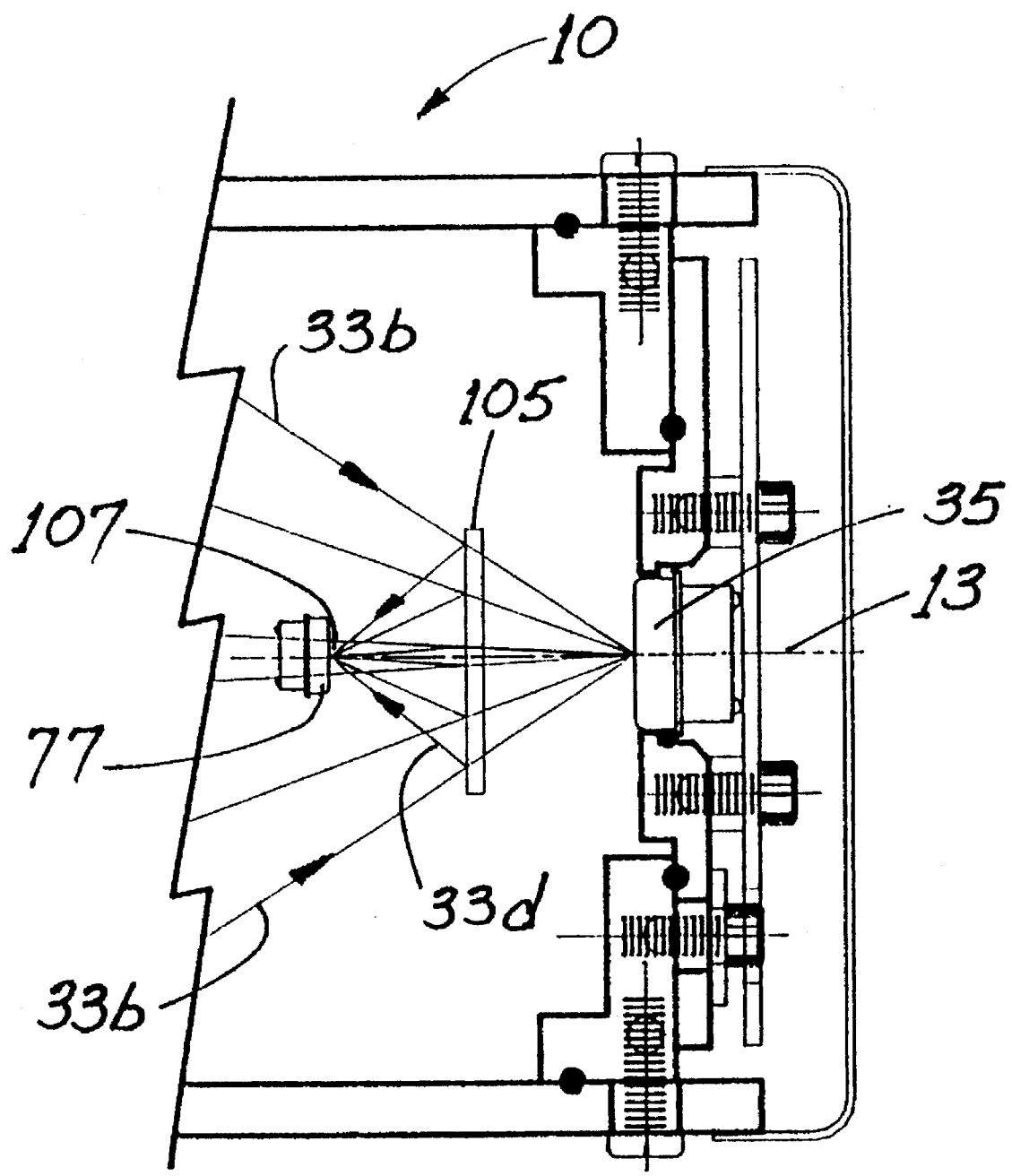
FIG. 8 is a view of the improved sensor similar to that of FIG. 2, with parts broken away, and illustrating yet another variant of the first embodiment of the sensor.

In yet another variant of the first embodiment, shown in FIG. 8, the sensor 10 has an extended particle-detection range. That is, it can detect particles 29 larger than those having a size below about 60–65% of the beam wavelength. The sensor 10 includes a beam splitter 105 having a relatively flat plate of ordinary optic-quality, uncoated glass of a thickness on the order of 1–1.5 mm. The splitter 105 reflects a few percent, e.g., 4%, of the light 33b impinging thereon and such reflected light 33d is directed to a secondary detector 77. The secondary detector 77 is preferably a low-gain detector selected to "process" reflected light pulses from particles 29 so large that such scattered and reflected light 33a, 33b would exceed the dynamic voltage range of the primary detector 35. The aforementioned plate thickness represents a reasonable compromise between acceptable plate cost and a plate which substantially avoids "double image" problems as may result when light reflects from both plate surfaces.

The detectors 35, 77 face one another, the splitter 105 is positioned between them and the splitter 105 and the detector 77 are generally normal to the major axis 13. And the secondary detector 77 is located coincident with the focal point 107 of the light beams 33d reflected by the splitter 105.

In operation, air drawn from a "clean room" and (inevitably) having at least a few particles 29 entrained therein flows into the proximal end 109 of the inlet tube 25 and is drawn away through the outlet tube 27. As a particle 29 passes through the view volume 95, the beam 31 strikes the particle 29 and light 33a is therefore scattered. A substantial portion of the scattered light 33a strikes the mirror 11 and is once-reflected to the primary detector 35. The resulting voltage signal is analyzed in a known way to provide information about particle size and about the number of particles 29 in, say, a cubic meter of clean room air.

The advantages of the first embodiment of the improved sensor 10 are several. With known sensors, the percentage of the particle-scattered light that is "collected" by the mirror and detector for analysis is in the low to middle 80's. In the first embodiment of the sensor 10, a scattered light collection percentage in the low 90's results. And when greater amounts of scattered light can be collected, the intensity of the beam 31 can be reduced. Such reduction is certainly not trivial. For example, higher intensity light sources costing $1000 or more are not unusual. With reasonable reduction in required beam intensity, the cost of the source 17 may be reduced by a factor of 10 or so.

However, situations involving extremely small particles and/or an elevated flow rate may require a high intensity light source. This is so since smaller particles have less area to reflect light and faster-moving particles are "in" the light beam for a shorter period of time. Either instance results in less reflected light and increasing the intensity of the light source is a way to help maintain the intensity of reflected light. This is desirable since such intensity must be sufficiently great that the light can be "sensed" by available detectors and the resulting detector signal must be sufficiently robust to be capable of analysis by available processing circuits and the like.

Figure 10:
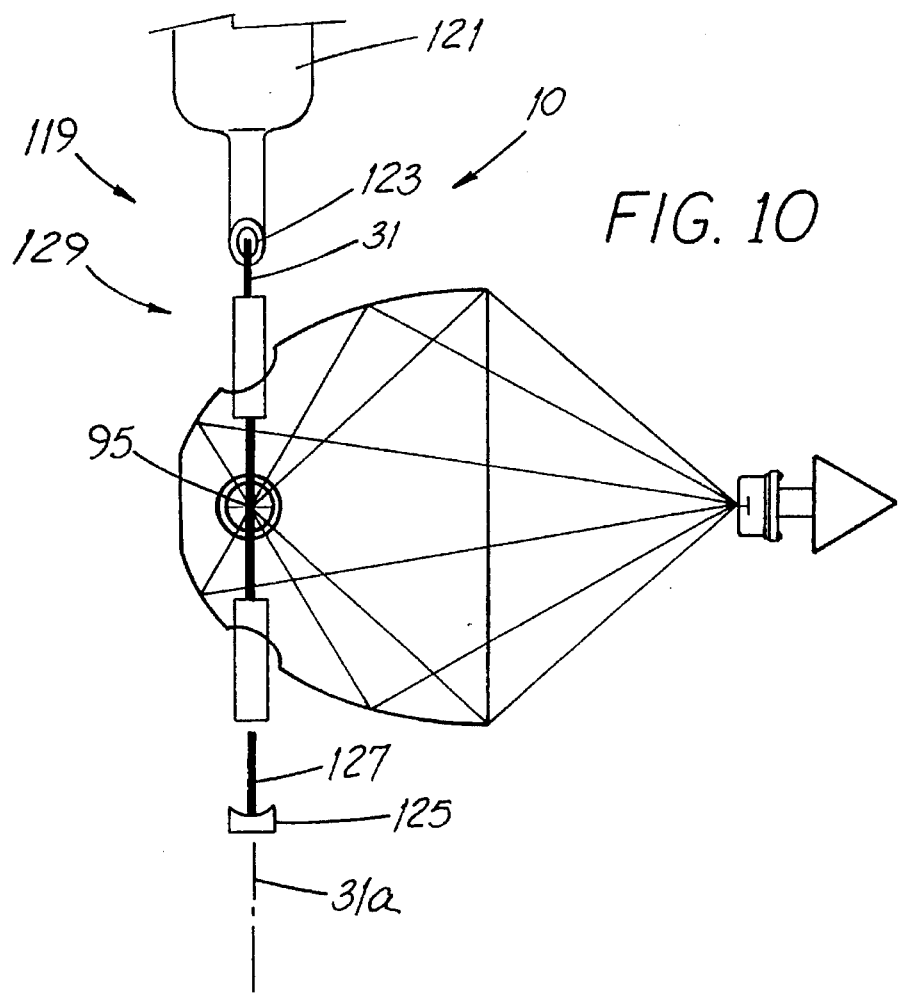
FIG. 10 is a view like that of FIG. 2 and showing yet another variant of the first embodiment of the sensor which uses an active cavity laser as a light source.

The sensor 10 of FIG. 10 corresponds generally to that of FIG. 2 except that the light source 17 and light trap 37 are replaced by a multi-mode active cavity helium-neon laser 119.

The laser 119 has a plasma tube 121 as a light source producing polarized light which exits the tube through the Brewster window 123 and propagates to the spherical output mirror 125 which completes the laser cavity 129. It should be understood that in this type of laser, the tube 121, the window 123 and the mirror 125 are all part of and define the cavity 129.

The mirror 125 reflects the light along the path 127 and back to the Brewster window 123, thereby greatly intensifying the magnitude of useable light at the view volume 95. It is to be appreciated that the variant arrangements shown in FIGS. 5–7 may be used in a sensor 10 having an active cavity laser 119 in place of the light source 17 and light trap 37 as illustrated.

Figure 11:
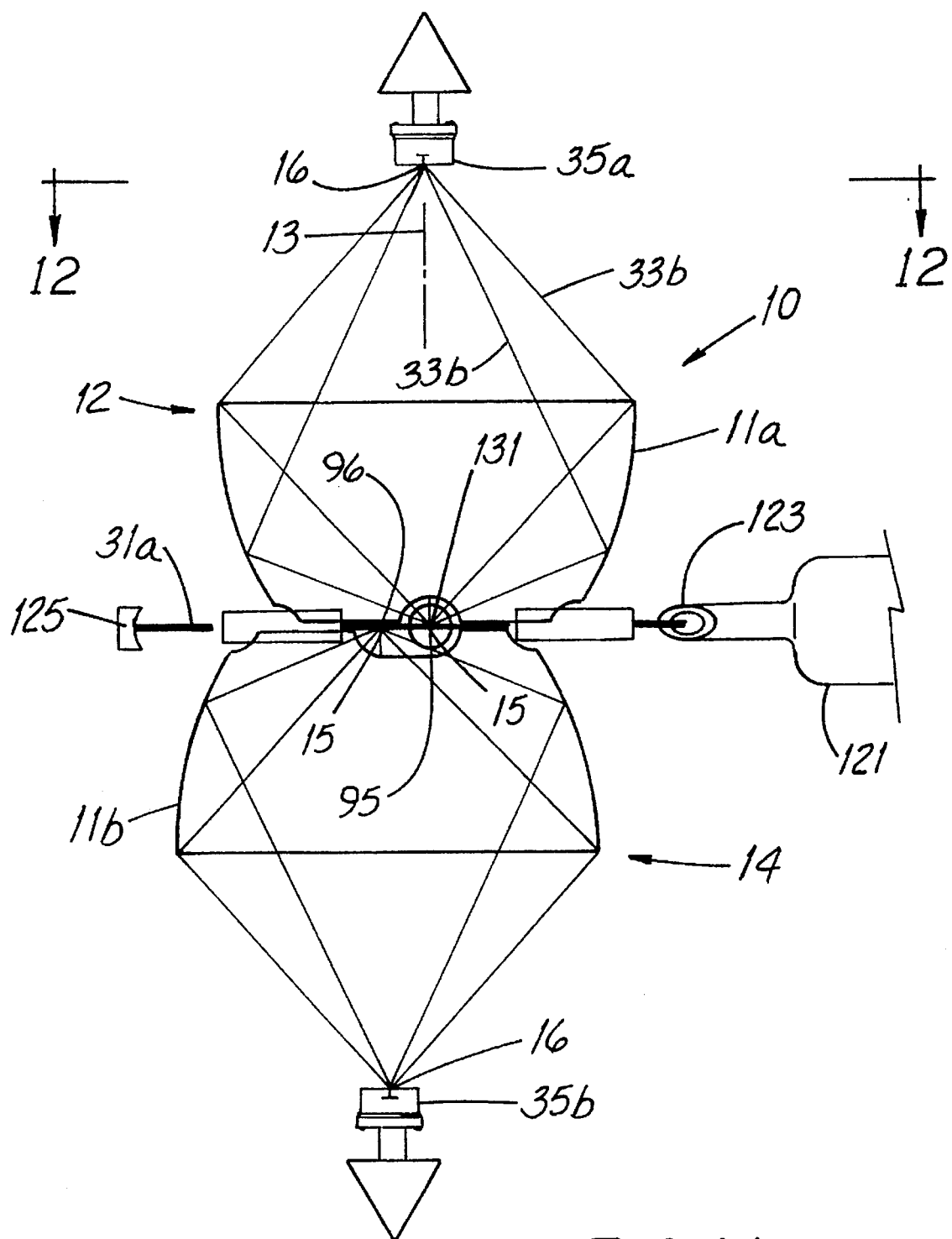
FIG. 11 is a view taken from the same general perspective of FIG. 2, with parts omitted, and showing that variant of the second embodiment of the sensor which uses two reflecting mirrors. Parts are omitted for clarity.
Figure 12:
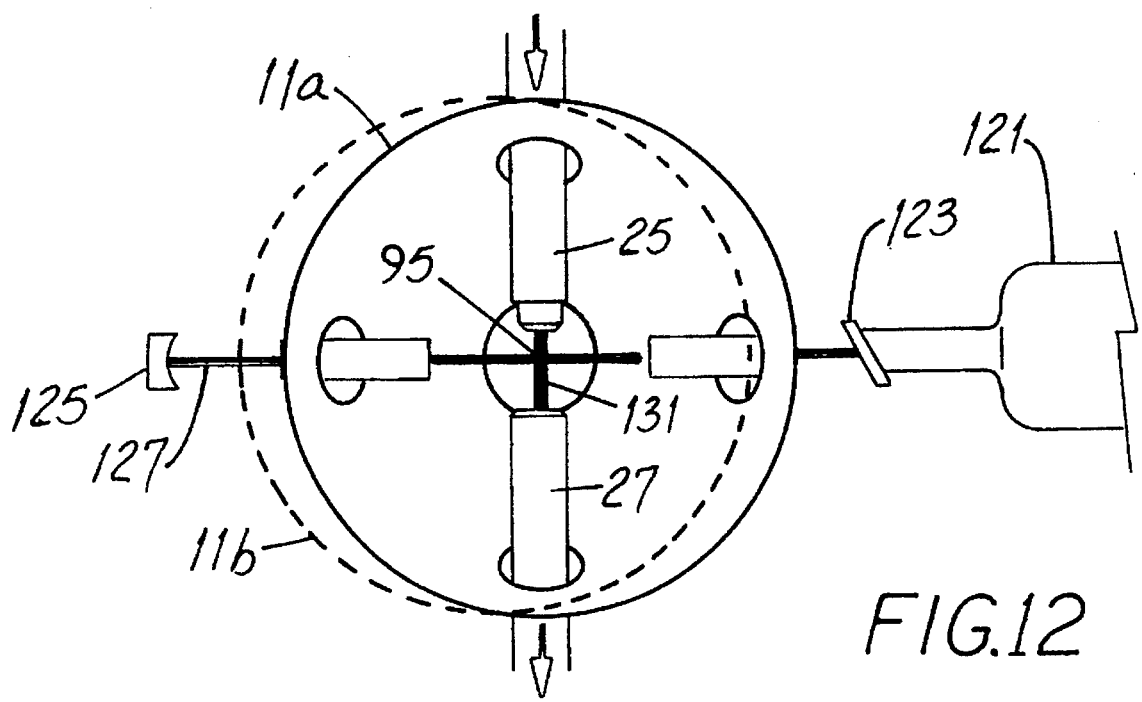
FIG. 12 is a view of the sensor of FIG. 11 taken from the perspective of viewing axes 12—12 of FIG. 11.
Figure 13:
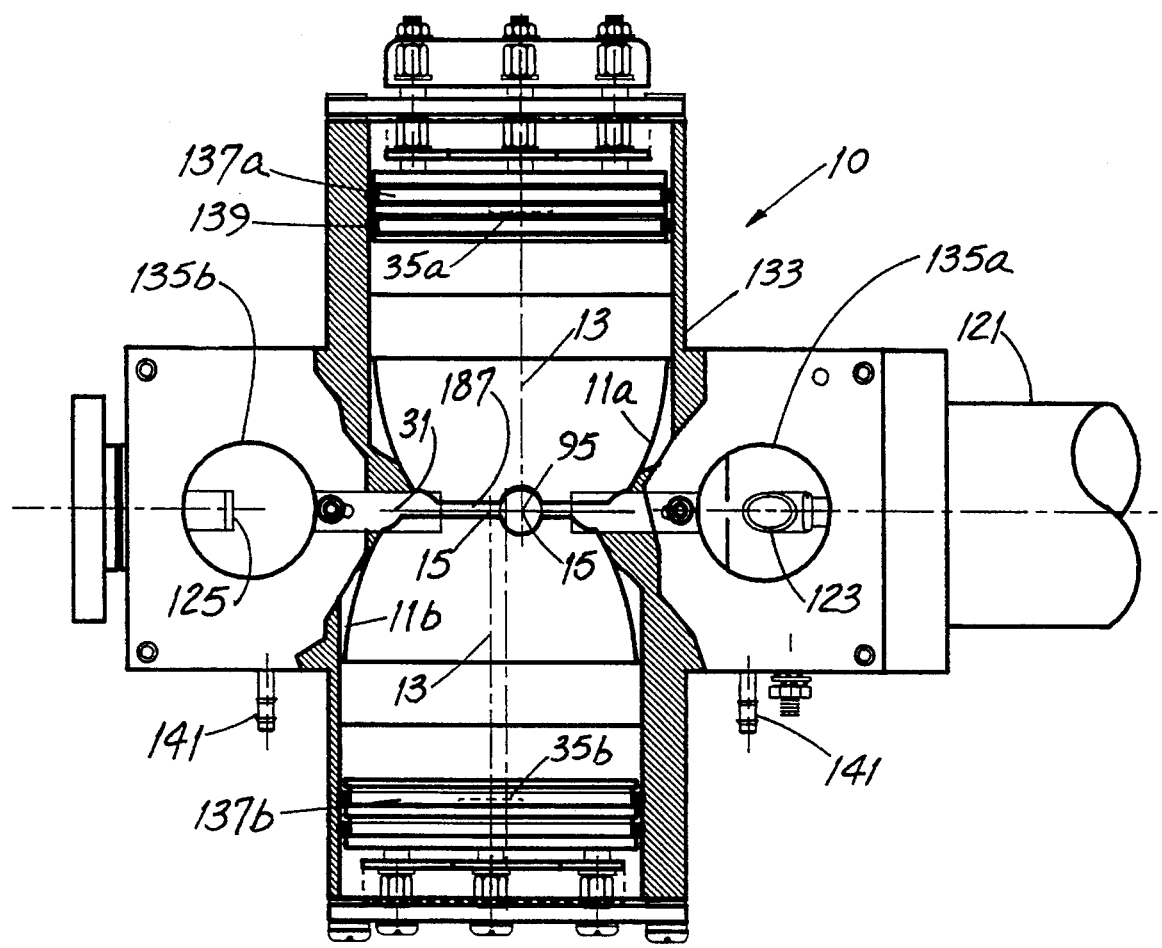
FIG. 13 is another view of the sensor of FIGS. 11 and 12 showing housing and other components thereof.

FIGS. 11–13 illustrate one variant of a second embodiment of the improved sensor 10; another variant of such embodiment is described below in connection with FIGS. 19 and 20.

The second embodiment has particular utility in neutralizing the effect of variations in laser power. The sensor 10 includes a multi-mode active cavity helium-neon laser 119 having a light beam 31 extending along a beam axis 31a Considered "three-dimensionally," the particle-carrying air flow path 131 extends out of the drawing sheet in the view of FIG. 11 and is coincident with the sheet in FIG. 12. Intersection of the beam 31 and the flow path 131 defines the view volume 95 as portrayed in FIG. 9. It is to be appreciated that the particle path 99 and the air flow path 131 are generally synonymous.

Referring to FIG. 13, the sensor 10 includes a housing 133 supporting the plasma tube 121 and the output mirror 125. The Brewster window 123 is visible through the access opening 135a while the mirror 125 is visible through access opening 135b. A cylinder 137a has double O-ring seals 139 and supports the first detector 35a at the secondary focal point 16. Similarly, a cylinder 137b supports the second detector 35b. Purge fittings 141 are provided so that the housing 133 can be filled with substantially particle-free air to avoid deposit of particles on the window 123 or output mirror 125.

As a first light-collecting apparatus 12, the sensor 10 includes a first elliptical mirror 11a and its primary focal point 15 and the view volume 95, sometimes referred to as a first locus, are coincident with one another. Light rays 33b (scattered by a particle 29 and by gas molecules adjacent to the particle 29) are once-reflected by the first mirror 11a and directed to and impinge upon a first detector 35a at the secondary focal point 16 of the mirror 11a. Both focal points 15, 16 are along the major axis 13 of the mirror. The first detector 35a provides a first output signal and the way such signal is used is described below.

As a second light-collecting apparatus 14, the sensor 10 also includes a second elliptical mirror 11b and its primary focal point 15, sometimes referred to as a second locus, is displaced along (and is coincident with) the beam axis 31a and therefore, is spaced from the view volume 95. This second locus may aptly be referred to as a "quasi view volume 96." Light rays (scattered by gas molecules but not by particles) are once-reflected by the second mirror 11b and directed to and impinge upon a second detector 35b at the secondary focal point 16 of the mirror 11b. Both focal points 15, 16 are along the major axis 13 of the second mirror 11b.

The second detector 35b similarly provides a second output signal.

Understanding of the following explanation will be aided by the following information and by recalling that the first mirror 11a reflects light scattered by both a particle 29 and by adjacent gas molecules 161. On the other hand, the second mirror 11b, having its primary focal point 15 spaced somewhat away from the particle path 99, does not "pick up" light scattered by a particle 29. However, such second mirror 11b does reflect light scattered by gas molecules 161 in the path of the light beam 31.

As background information, presently-available laser light sources vary slightly in power output and light intensity varies with it. The light received by the first detector 35a (scattered by a particle 29 and by gas molecules 161) and that received by the second detector 35b (scattered only by gas molecules 29) both evidence, by the same changes in "scattering signal" strength, such variations in laser power. But varying laser power is not the only problem facing the designer of a highly sensitive particle sensor.

Detectors (like detectors 35a and 35b) used to "sense" reflected light are randomly struck by light photons. Such photons cause the detector to exhibit what is commonly referred to as "shot noise," an unwanted low-level, random electronic pulse or "hash" which impairs the quality of the detector output signal. And even in the absence of light photons impinging thereon, presently-available detectors exhibit random electronic noise which is referred to herein as "detector noise" as distinguished from photon-caused "shot noise."

Figure 14:
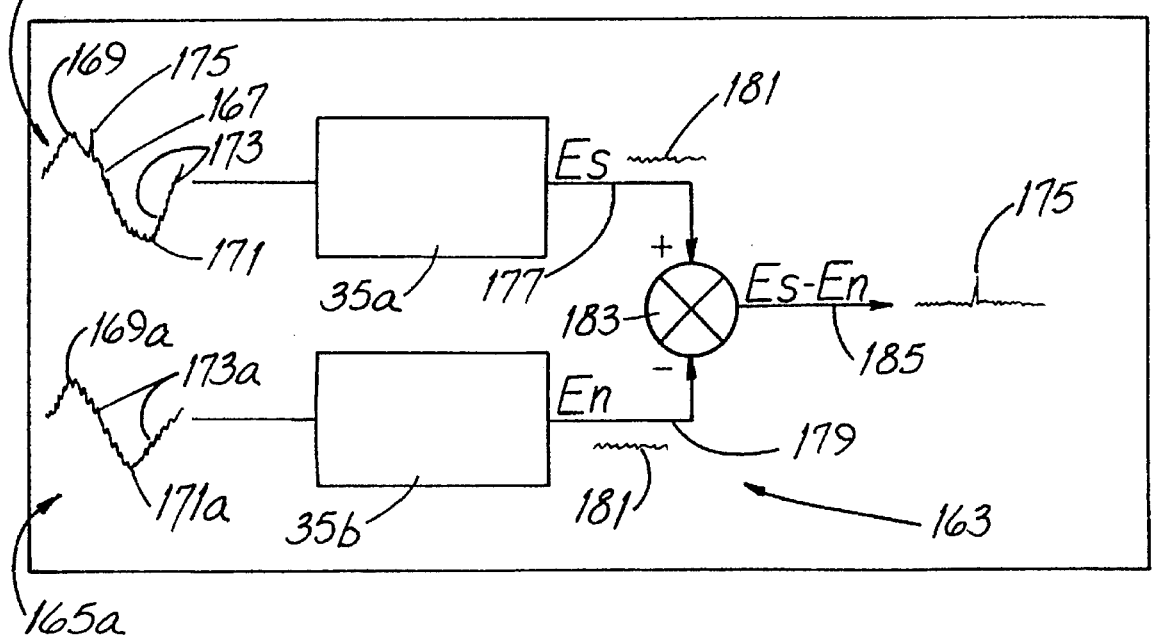
FIG. 14 is a simplified diagram of a signal processing circuit.

FIG. 14 shows a block diagram processing circuit 163 used to detect a particle 29. As explained above, the intensity of light scattered by gas molecules 161 will vary with minute variations in laser power which occur over time. Such variations occur in any laser (like laser 119) now known. Since a particle 29 flying through the light beam 31 is exposed to light for but an instant, such power variations are not noticeable as to a particular particle 29.

The first composite waveform 165 represents variations in laser output power (the waveform 167 having one peak 169 and one valley 171) and also represents (by the several low-amplitude ripples 173 on the waveform 167) light scattered by gas molecules 161 in the view volume 95. Such composite waveform 165 also includes a brief "blip" 175 representing light scattered in the view volume 95, i.e., at the first locus, by a particle 29. This blip 175 is very brief since, it will be recalled, a particle 29, "flying" along a path 99 at relatively high velocity, is in the view volume 95 for an extremely short time. Light represented by the first composite waveform 165 is reflected to the first detector 35a by the first mirror 11.

The second composite waveform 165a similarly represents variations in laser output power (the waveform having one peak 169a and one valley 171a) and also represents (by the several low-amplitude ripples 173a on the waveform 165a) light scattered by gas molecules 161 in the quasi view volume 96. However, the second composite waveform 165a does not include the "blip" 175 representing light scattered in the view volume 95 by the particle 29. Since the first focal point 15 of the second mirror 11b is displaced slightly from the particle path 99. The light scattered at the second locus (i.e., in the quasi view volume 96) by gas molecules 161 is reflected by the second mirror 11b to the second detector 35b.

Light (represented by the composite waveforms 165 and 165a) strike the detectors 35a and 35b, respectively, and cause each such detector to responsively generate an output signal Es and En, respectively, which are propagated along lines 177, 179, respectively. However, it will be recalled that detectors produce both detector noise and shot noise and such noise is represented by the small-amplitude lines 181. Therefore, the signals propagated along the lines 177 and 179 by the detectors 35a and 35b, respectively, each have characteristics representing (a) variations resulting from changes in laser power (b) detector noise and (c) shot noise. However, only the signal propagated along the line 177 has a characteristic, i.e., the blip 175, representing light scattered in the view volume 95 by a particle 29.

It should be observed that the variations in the waveforms 167, 167a represented by the peaks 169, 169a and the valleys 171, 171a have a magnitude much greater than that of the low-amplitude ripples 173, 173a. The significance of this fact is that variations resulting from changes in laser power are much more likely to impair sensor sensitivity by "swamping out" the particle blip 175 than are detector noise and shot noise.

Referring further to FIG. 13, the first output signal Es of the first detector 35a and the second output signal En of the second detector 35b are directed to a subtraction circuit 183 where they are processed. Such circuit 183 (which is well-known per se) "removes" from that signal propagated on the line 177 the waveform propagated on the line 179 and resulting from variations in laser power and from light scattered by gas molecules 161. The resulting circuit output signal "Es-En" along line 185 is relatively "clean" and represents substantially only light scattered by the airborne particle 29 (the "blip" 175) accompanied by detector noise and shot noise, both of which are at a low level compared to that portion of the signal representing the airborne particle 29.

Some of the more technically-elegant aspects of the second embodiment of the sensor 10 should be noted and appreciated. For example, the gas molecules 161 in the cavity 187 are at the same pressure and have the same composition, irrespective of whether they are at the view volume 95 or the quasi view volume 96. This negates the effect of gas pressure or gas composition changes upon the light impinging on the detectors 35a, 35b and upon the output signal Es-En.

And gas molecules 161 at the view volume 95 and at the quasi view volume 96 are subjected to identical variations in the intensity of the light striking such molecules 161 that may result from variations in laser power. That is to say, there is no need to "compensate" any of the output signals Es, En or Es-En because of gas pressure, gas composition or light intensity changes. Thus, the second embodiment of the sensor 10 enables construction of a highly-sensitive particle counter especially well suited for particle path flow rates of about 1 CFM and for detecting particles 29 flowing along such paths 99 of about 0.1 micron and smaller.

The following Table will be helpful in making a particle counter having a particular particle sensitivity and particle path flow rate:

| PARTICLE SENSITIVITY | FLOW RATE | LIGHT SOURCE |
| --- | --- | --- |
| 0.1 μm or smaller | 1 CFM | HeNe mutimode active cavity or 1 W IR Laser Diode |
| 0.2 μm | 1 CFM | 20 MW IR Laser Diode |
| 0.3 μm or larger | 1 CFM | ≦mW IR/visible Laser Diode |
| 0.05 μm | 0.1 CFM | fractional Watt visible laser or small beam, high power HeNe |

The following information will be helpful in appreciating additional aspects of the improved sensor 10. Using the wavelength of the illuminating beam 31 as a measurement "yardstick," particles 29 of a size nominally equal to or slightly larger than such wavelength tend to scatter more light in a forward direction, i.e., in the direction of beam "travel" and along paths relatively close to the beam.

As particles 29 become smaller with respect to such wavelength, light scattered by them tends to be scattered rather equally forward and backward but nevertheless along paths relatively close to the beam 31. And for particle sizes below about 25–30% of the beam wavelength, the amount of light scattered laterally (rather than forward and backward) is very small.

In FIGS. 2 and 7, it will be noted that some scattered light 33a will travel along paths represented by the arrows 111, will not strike the mirror 11 and therefore will not be reflected to the detector 35 for analysis. From the explanation set forth above, and from FIG. 15 it will be appreciated that with particles 29 which are relatively small compared to light wavelength, most light 33a scattered by the particle 29 is, in general, directed forward or backward as represented by the arrows 115. Relatively little light is scattered laterally as represented by the arrows 113a, 113b, respectively. Therefore, light travelling laterally along paths represented by the arrows 113a, 113b constitutes a very small percentage of the total scattered light.

Figure 16:
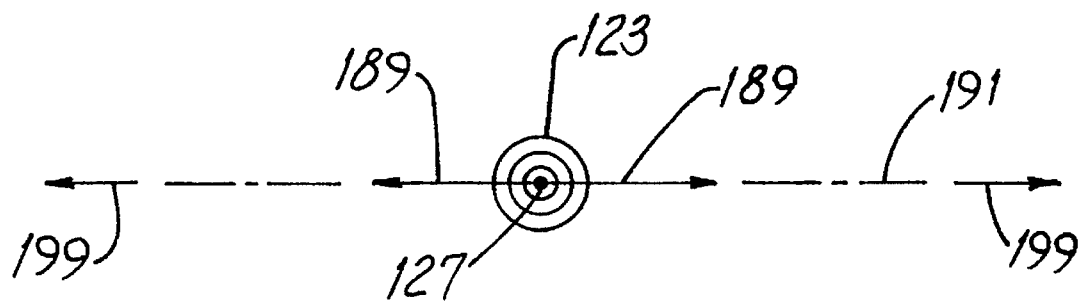
FIG. 16 is a diagram showing polarized light emitted by an active cavity laser.

In a sensor 10 using an active cavity laser 119 having a Brewster window 123, light emanating therefrom is polarized as represented by the arrows in FIG. 16. However, when such polarized light strikes a particle 29, the light tends to be reflected in many different directions, albeit at widely differing intensities consistent with FIG. 15 and the above explanation.

Figure 15:
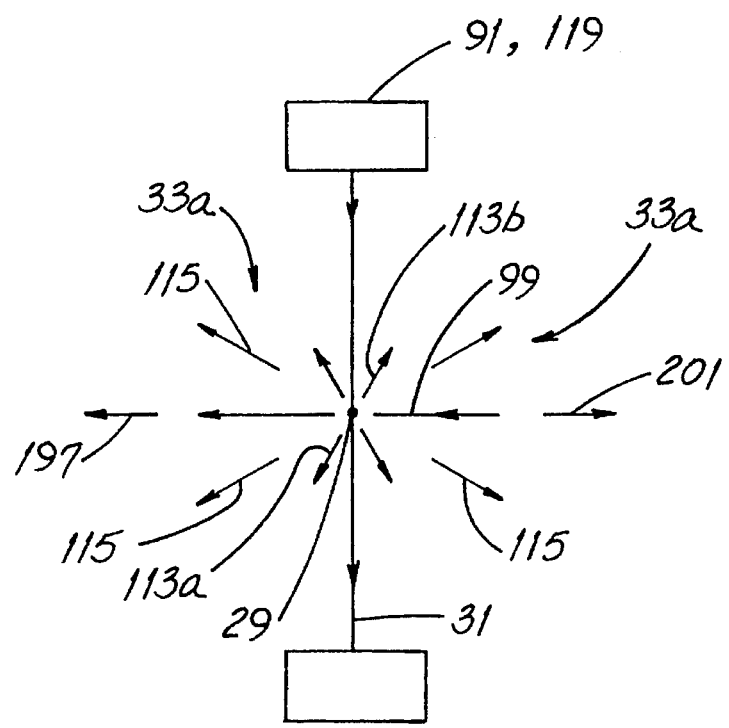
FIG. 15 is a simplified light scattering diagram.
Figure 17:
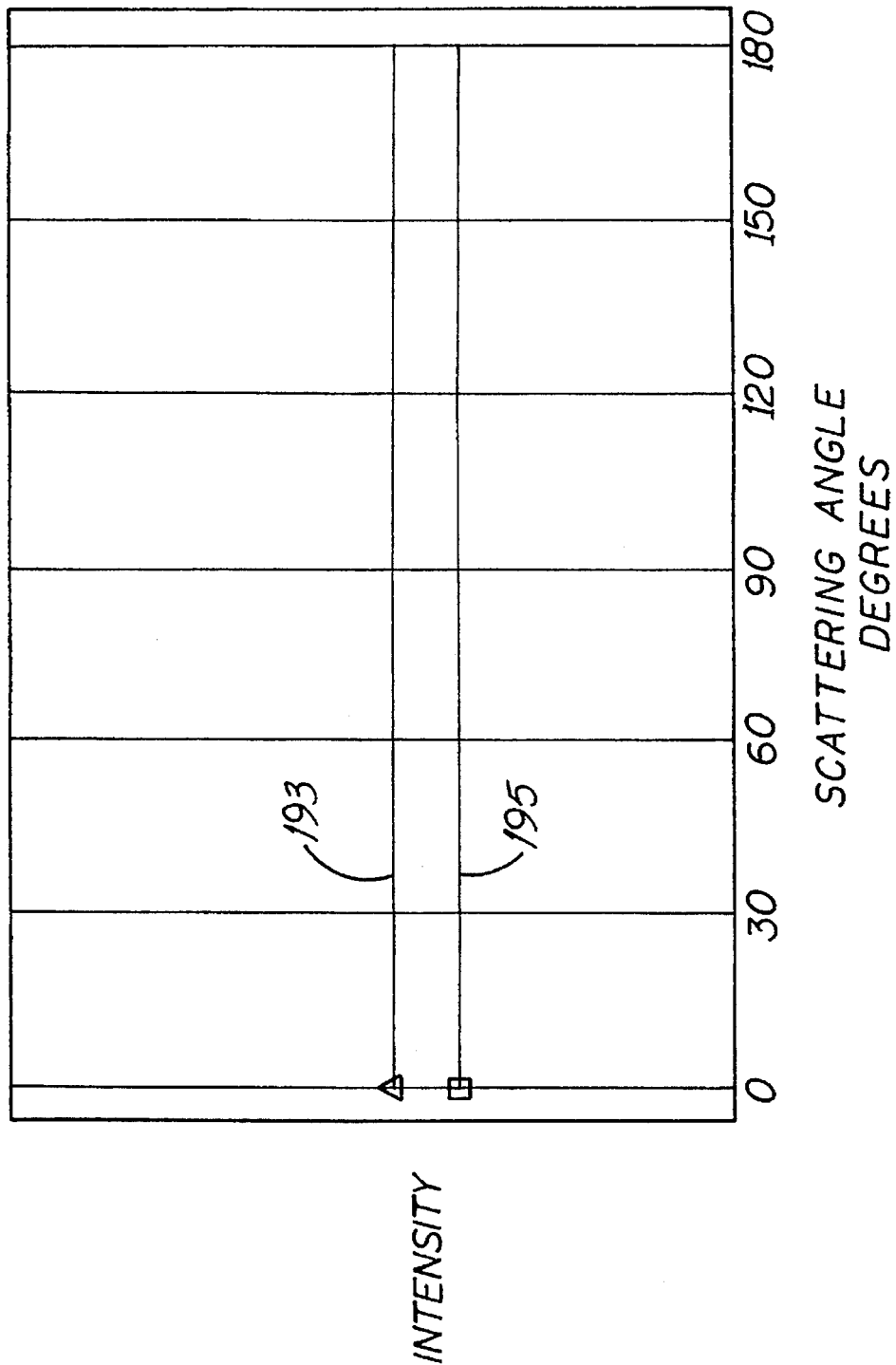
FIG. 17 is a graph showing angular light scattering intensity for perpendicularly polarized light.

For this part of the description, it will be assumed that the plane of polarization 191 is coincident with the drawing sheet showing FIG. 15. FIG. 17 illustrates the angular scattered intensity for light polarized (by reflection from the particle 29) perpendicular to the plane 191 shown in FIG. 16, i.e., into and out of the paper when considering FIG. 15. The line 193 represents light scattered by a 0.1 micron particle 29 while the line 195 represents light scattered by a 0.0633 micron particle 29. It is apparent that for perpendicular polarized light, the intensity is substantially constant, irrespective of scattering angle where (in FIG. 17) 0° scattering angle is in the forward direction represented by the arrow 197, 90° scattering angle is in the direction represented by the arrows 199 and 180° scattering angle is in the direction represented by the arrow 201.

Figure 18:
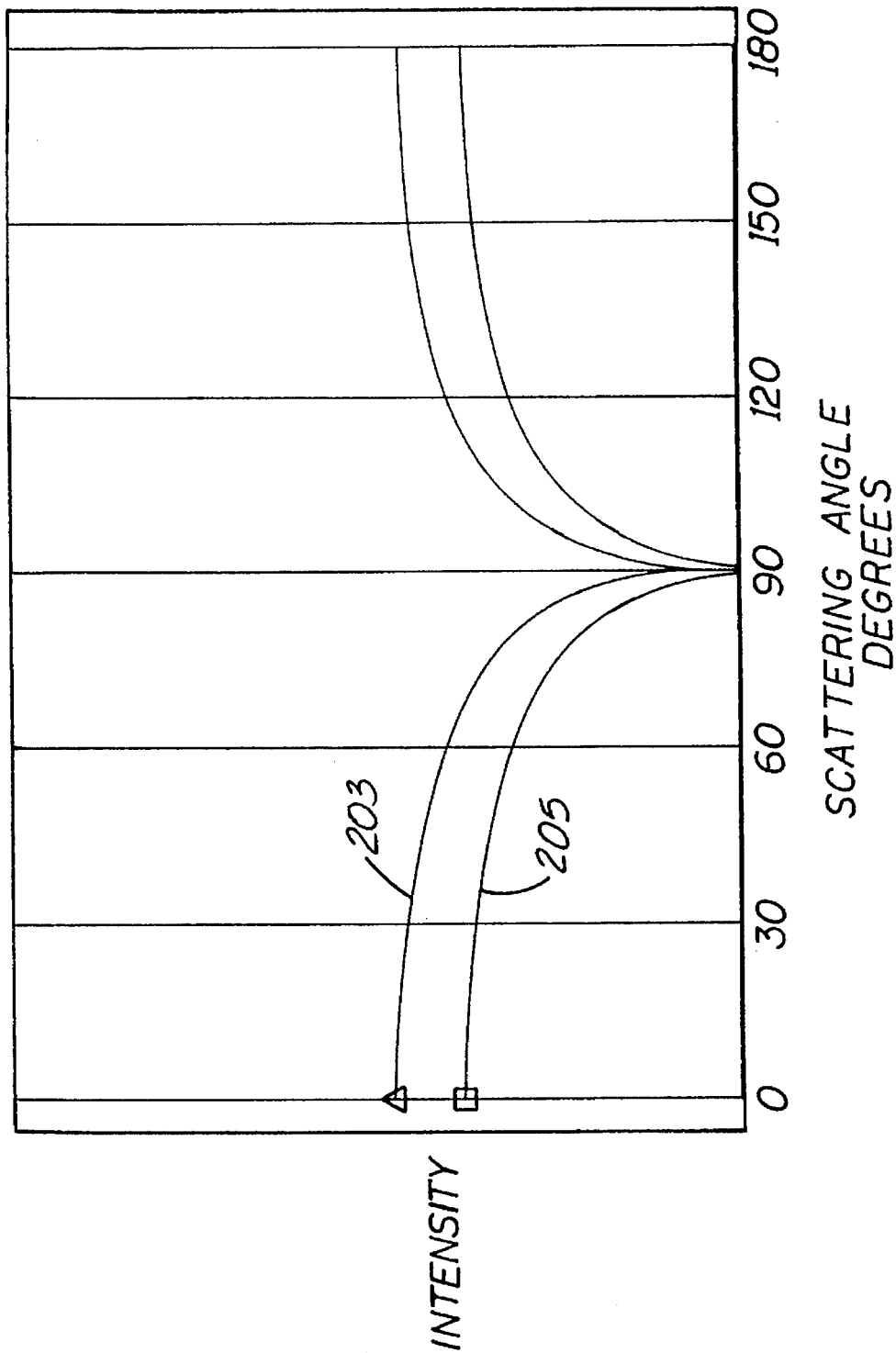
FIG. 18 is a graph showing angular light scattering intensity for parallel polarized light.

FIG. 18 illustrates the angular scattered intensity for light polarized (as before, by reflection from the particle 29) but parallel to the plane 191 shown in FIG. 16, i.e., coincident with the paper when considering FIG. 15. The line 203 represents light scattered by a 0.1 micron particle 29 while the line 205 represents light scattered by a 0.0633 micron particle 29. It is apparent that for parallel polarized light, the intensity is greatest in the forward and backward directions (represented in FIG. 15 by the arrows 197 and 201, respectively) and is very small as the scattering angle approaches 90°. And at a scattering angle of 90°, for example, intensity changes depending upon the particular angle of polarization under consideration.

Thus, locating the inlet tube 25 at the rear portion of the mirror 11, 11a as shown in FIG. 7 or 11 works little impairment to the light gathering qualities of the sensor 10. This is so since at least for parallel polarized light, such rear portion receives and reflects relatively little light.

Figure 19:
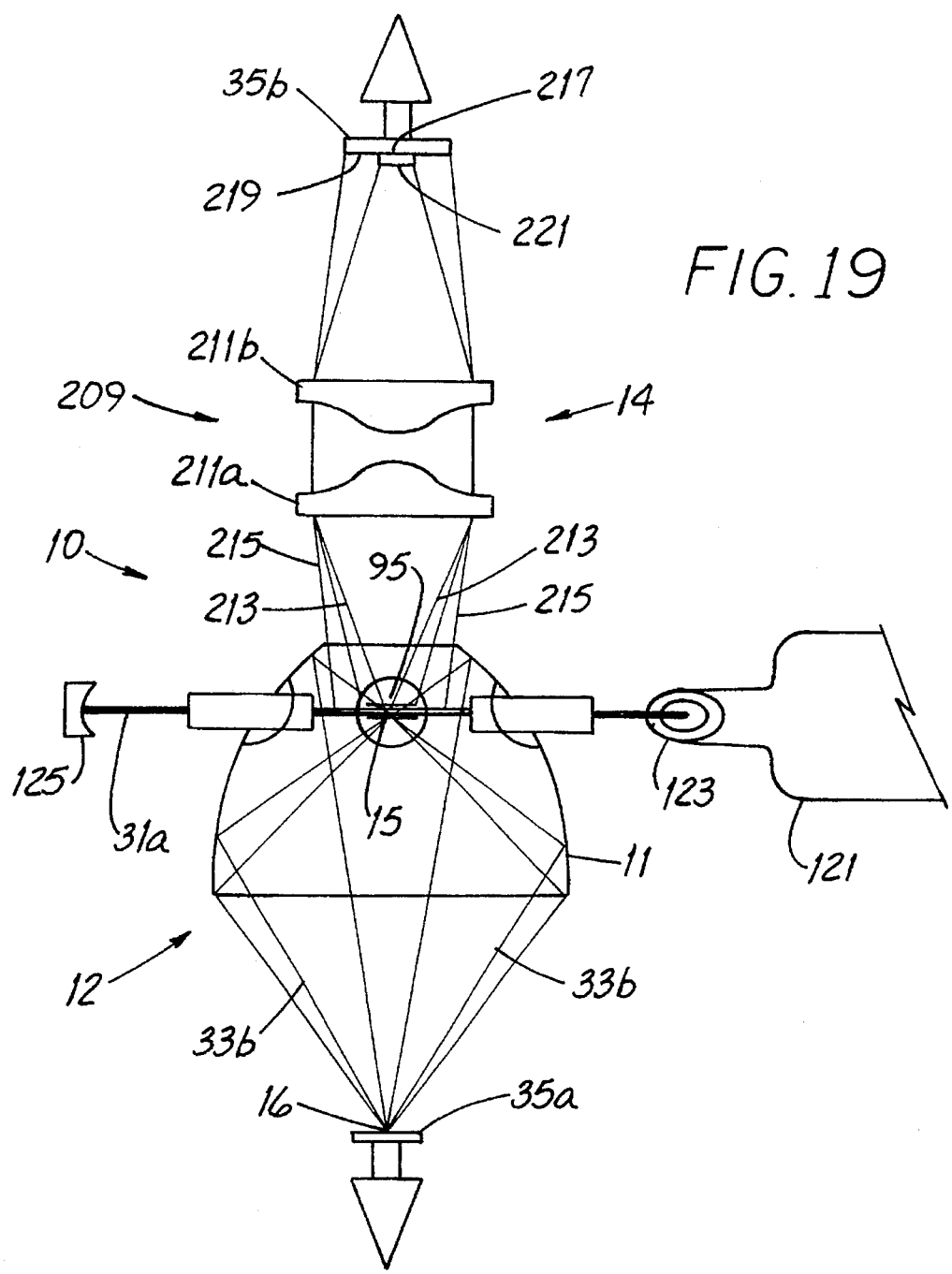
FIG. 19 is a view of another variant of the second embodiment of the sensor which uses one light reflecting system and one light imaging system. Parts are omitted for clarity and the viewing volume is greatly enlarged.
Figure 20:
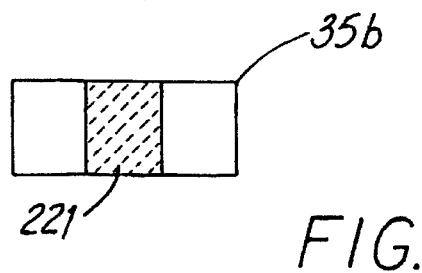
FIG. 20 is an enlarged view of a portion of the detector of the sensor of FIG. 19 and illustrating an opaque mask blocking a portion of the detector.

FIGS. 19 and 20 depict another variant of the second embodiment of the sensor 10. As a first light-collecting apparatus 12, the sensor 10 includes an elliptical mirror 11 having its primary focal point 15 coincident with the view volume 95. In other respects, the arrangement of the mirror 11 and its detector 35a are substantially identical to the arrangement of the mirror 11a and detector 35a shown in FIG. 11 and described in connection therewith.

As a second apparatus 14 collecting light scattered substantially only by gas molecules 161, the sensor 10 has an imaging system 209 including at least one lens 211. In a highly preferred arrangement, such system 209 has a pair of lenses 211a, 211b which may be fresnel lenses (preferred), aspheric lenses or spheric lenses. A short lens focal length is preferred for best light-gathering properties. Lenses 211a, 211b gather and focus light reflected from (as portrayed in FIG. 9) a particle 29 and from gas molecules 161.

It is to be noted that the light rays 213, emerging from the center of the viewing volume 95, represent light reflected by a particle 29 while rays 215, emerging from locations away from such center, represent light reflected by gas molecules 161. To put it another way, the "image" of the view volume 95 is projected toward the surface of the detector 35b. Rays representing light reflected by the particle 29 will strike the detector 35b near its central portion 217 while rays representing light reflected by gas molecules 161 strike such detector 35b nearer the perimeter 219.

In a highly preferred arrangement, the detector 35b is configured to provide a signal representing only light scattered by gas molecules 161. To that end, the detector 35b includes an opaque mask 221 over its central portion 217. The mask 221 blocks light reflected by the particle 29 but permits light reflected by gas molecules 161 to strike the detector 35b. The detector 35b thus provides a "molecules-only" signal which is subtracted from the signal representing light reflected by both the particle 29 and molecules 161.

While the principles of the invention have been described in connection with specific embodiments, they are shown and described by way of example and are not intended to limit the invention.

We claim:

1. In a particle sensor containing gas molecules and including (a) a first elliptical mirror with a cavity, a first major axis and primary and secondary focal points along such first major axis, (b) a particle-illuminating beam of light having a wavelength and extending along a beam axis intersecting the primary focal point, and (c) an inlet for introducing airborne particles into a sensor view volume, the improvement wherein:

a light detector is at the secondary focal point;

the region between the primary focal point and the light detector is substantially unobstructed;

the primary focal point of the first mirror is coincident with the view volume;

the sensor includes a second mirror having a second major axis offset along the beam axis and spaced from the first major axis, the second mirror reflecting light scattered substantially only by gas molecules; and the beam axis and the first major axis define an angle greater than 0° therebetween;

whereby particles having a maximum dimension substantially less than the wavelength are detected.

2. The sensor of claim 1 wherein the beam axis and the first major axis define and included angle not greater than 90°.

3. The sensor of claim 1 wherein the beam of light is used to assay particles, particles are introduced along the path, and a path and the beam axis defined an included angle of less than 90°.

4. The sensor of claim 1 including a light trap and wherein the light beam has a wavelength and the light trap comprises a plate absorbing unwanted, non-scattered light of that wavelength.

5. The sensor of claim 4, wherein the plate is outside the cavity and is angularly oriented with respect to the beam axis.

6. The sensor of claim 5 wherein the plate comprises a light bandpass filtered having a nominal bandpass wavelength range and the wavelength of the beam of light is outside the nominal bandpass wavelength.

7. The sensor of claim 1 including a light trap and wherein the light beam has a wavelength and the light trap comprises a primary plate absorbing non-scattered light of that wavelength and further comprises a secondary plate absorbing unwanted light reflected from the primary plate.

8. The sensor of claim 1 wherein the second mirror has a primary focal point displaced along the beam axis.

9. The sensor of claim 8 wherein the second major axis of the second mirror is substantially parallel to the first major axis of the first mirror.

10. The sensor of claim 1 wherein light is scattered in the view volume by airborne particles and by gas molecules and wherein:

the light detector is a first detector receiving light scattered by an airborne particle and by gas molecules and providing a first detector signal;

and the sensor also includes:

a second detector receiving light scattered substantially only by gas molecules and reflected by the second mirror, the second detector providing a second detector signal; and, the first detector signal and the second detector signal are processed in a subtraction circuit providing an output signal representing substantially only light scattered by an airborne particle.

11. The sensor of claim 10 wherein:

the first mirror has a major axis;

the first detector is coincident with the major axis of the first mirror;

the second mirror has a major axis; and, the second detector is coincident with the major axis of the second mirror.

12. An improved particle sensor comprising:

a light beam extending along a beam axis;

a particle flow path intersecting the beam axis and defining a view volume therewith;

a first apparatus collecting light scattered by an airborne particle and by gas molecules; and, a second apparatus collecting light scattered substantially simultaneously and substantially only by gas molecules.

13. The sensor of claim 12 including first and second detectors and wherein:

the first apparatus includes a mirror;

light scattered by an airborne particle and by gas molecules and reflected by the mirror impinges on the first detector providing a first output signal;

light scattered substantially only by gas molecules and collected by the second apparatus impinges on the second detector providing a second output signal; and, the sensor includes a circuit subtracting the signals.

14. The sensor of claim 13 wherein the first output signal and the second output signal each include components resulting from (a) shot noise, (b) random detector noise and (c) changes in laser power ad the circuit substrates from the first output signal that component of the second output signal resulting from changes in laser power.

15. The particle sensor of claim 12 wherein:

the second apparatus is free of mirrors and comprises an imaging system having at least one lens.

16. The particle sensor of claim 15 wherein the second apparatus includes a detector having a central portion and an opaque mask preventing scattered light from striking the central portion.

17. The particle sensor of claim 12 wherein the second apparatus comprise an imaging system having at least one lens far collecting light scattered by an airborne particle and by gas molecules.

18. The particle sensor of claim 17 wherein the second apparatus includes a detector and an opaque mask substantially preventing light scattered by an airborne particle from striking the detector.

19. A method for assaying a particle illuminated by a light beam and including the steps of:

detecting a first quantum of light scattered by a particle and by gas molecules;

detecting a second quantum of light scattered substantially simultaneously and substantially only by gas molecules.

20. The method of claim 19 wherein:

the step of detecting the first quantum of light includes reflecting the first quantum of light from a first mirror;

the step of detecting the second quantum of light includes reflecting the second quantum of light from a second mirror.

21. The method of claim 20 wherein:

the first quantum of light is scattered at a first locus;

the second quantum of light is scattered at a second locus;

each mirror has a focal point;

the focal point of the first mirror is at the first locus; and, the focal point of the second mirror is at the second locus.

22. The method of claim 20 further including the step of:

generating a first signal representing the first quantum of light;

generating a second signal representing the second quantum of light; and subtracting the signals.

23. The method of claim 22 wherein the step of generating a first signal includes:

providing an elliptical first mirror having a primary and a secondary focal point, the first mirror reflecting scattered light to a first detector at the secondary focal point of the first mirror;

and the step of generating a second signal includes:

providing an elliptical second mirror having a primary and a secondary focal point, the second mirror reflecting scattered light to a second detector at the secondary focal point of the second mirror.

24. The method of claim 19 wherein the second quantum of light is detected by imaging it toward a detector.

25. The method of claim 24 wherein the detector includes a central portion and the step of detecting a second quantum of light includes preventing scattered light from being received at the central portion 26. An improved particle sensor comprising:

a light beam extending along a beam axis;

a particle flow path intersecting the beam axis and defining a view volume therewith;

a first apparatus including a light-reflecting mirror having a focal point substantially coincident with the view volume and collecting light scattered by an airborne particle and by gas molecules; and, a second apparatus comprising (a) an imaging system having at least one lens collecting light scattered by an airborne particle and by gas molecules, and (b) a detector having an opaque mask preventing light scattered by an airborne particle from striking the detector, the detector thereby detecting light scattered substantially only by gas molecules.

27. A method for assaying a particle illuminated by a light beam and including the steps of:

detecting a first quantum of light scattered at a first locus by a particle and by gas molecules;

reflecting the first quantum of light from a first mirror having a focal point at the first locus;

detecting a second quantum of light scattered at a second locus substantially only by gas molecules;

reflecting the second quantum of light from a second mirror having a focal point at the second locus.

28. The method of claim 27 including the steps of:

generating a first signal representing a first quantum of light;

generating a second signal representing the second quantum of light; and subtracting the signals, and wherein the step of generating a first signal includes:

providing an elliptical first mirror having a primary and a secondary focal point, the first mirror reflecting scattered light to a first detector at the secondary focal point of the first mirror;

and the step of generating a second signal includes:

providing an elliptical second mirror having a primary and a secondary focal point, the second mirror reflecting scattered light to a second detector at the secondary focal point of the second mirror.

* * * * *

UNITED STATES PATENT AND TRADEMARK OFFICE
CERTIFICATE OF CORRECTION

PATENT NO. : 5,467,189
DATED : November 14, 1995
INVENTOR(S) : Gerhard Kreikebaum and David L. Chandler It is certified that error appears in the above-indentified patent and that said Letters Patent is hereby corrected as shown below:

In column 15, line 65, delete "unobstructured" and insert --unobstructed--.

In column 16, line 13, delete "the" and insert --a--.

In column 16, line 14, delete "a" and insert --the--.

In column 16, line 14, delete "defined" and insert --define--.

In column 16, line 24, delete "filtered" and insert --filter--.

In column 17, line 16, delete "ad" and insert --and--.

In column 17, line 16, delete "substrates" and insert --subtracts--.

Signed and Sealed this

Nineteenth Day of March, 1996

BRUCE LEHMAN

*Attest:*

*Attesting Officer*        *Commissioner of Patents and Trademarks*